(12) United States Patent
Van Liesdonk et al.

(10) Patent No.: US 11,188,672 B2
(45) Date of Patent: Nov. 30, 2021

(54) LOCATION TRACKING ENABLING PRIVACY PROTECTION

(71) Applicant: KONINKLIJKE PHILIPS N.V., Eindhoven (NL)

(72) Inventors: Peter Petrus Van Liesdonk, Eindhoven (NL); Meilof Geert Veeningen, Eindhoven (NL); Supriyo Chatterjea, Eindhoven (NL)

(73) Assignee: Koninklijke Philips N.V., Eindhoven (NL)

( * ) Notice: Subject to any disclaimer, the term of this patent is extended or adjusted under 35 U.S.C. 154(b) by 58 days.

(21) Appl. No.: 16/555,336

(22) Filed: Aug. 29, 2019

(65) Prior Publication Data

US 2020/0082113 A1 Mar. 12, 2020

Related U.S. Application Data

(60) Provisional application No. 62/729,500, filed on Sep. 11, 2018.

(51) Int. Cl.
| | |
|---|---|
| *G06F 21/62* | (2013.01) |
| *G06F 16/29* | (2019.01) |
| *G06F 16/25* | (2019.01) |
| *H04L 9/08* | (2006.01) |
| *H04L 9/00* | (2006.01) |
| *H04L 9/06* | (2006.01) |
| *G06K 7/10* | (2006.01) |

(52) U.S. Cl.
CPC ........ *G06F 21/6227* (2013.01); *G06F 16/252* (2019.01); *G06F 16/29* (2019.01); *G06K 7/10366* (2013.01); *H04L 9/008* (2013.01); *H04L 9/065* (2013.01); *H04L 9/085* (2013.01); *H04L 9/0894* (2013.01)

(58) Field of Classification Search
CPC .... G06F 21/6227; G06F 16/252; G06F 16/29; G06K 7/10366; H04L 9/008; H04L 9/065; H04L 9/085; H04L 9/0894
See application file for complete search history.

(56) References Cited

U.S. PATENT DOCUMENTS

| | | | |
|---|---|---|---|
| 8,139,945 B1 | 3/2012 | Israel et al. | |
| 2004/0046667 A1* | 3/2004 | Copley | G08B 21/0286 340/573.4 |

(Continued)

OTHER PUBLICATIONS

Damgard, I. et al. "Practical Covertly Secure MPC for Dishonest Majority—or: Breaking the SPDZ Limits". ESORICS 2013, pp. 1-18.

(Continued)

*Primary Examiner* — Yonas A Bayou

(57) ABSTRACT

Some embodiments are directed to location-tracking system (100) comprising a location database (120) configured to receive a plurality of location updates from a plurality of tracking devices (112, 113), the plurality of location updates indicating the location of one or more objects, the location updates being stored encrypted with a cryptographic database encryption-key (130), multiple location-analysis devices execute a multi-party computation protocol on the encrypted location updates using a stored key-share, thus jointly computing a location-analysis result secret-shared among the multiple location analysis devices.

18 Claims, 6 Drawing Sheets

(56) References Cited

U.S. PATENT DOCUMENTS

| | | | | |
|---|---|---|---|---|
| 2005/0141345 | A1* | 6/2005 | Holm | G01S 7/003 |
| | | | | 367/99 |
| 2005/0251865 | A1* | 11/2005 | Mont | H04L 9/3073 |
| | | | | 726/26 |
| 2008/0065701 | A1* | 3/2008 | Lindstrom | G06F 16/258 |
| 2008/0126126 | A1* | 5/2008 | Ballai | G16Z 99/00 |
| | | | | 705/2 |
| 2009/0251289 | A1* | 10/2009 | Amtmann | H04L 63/0869 |
| | | | | 340/10.1 |
| 2010/0014676 | A1* | 1/2010 | McCarthy | H04L 9/30 |
| | | | | 380/277 |
| 2011/0252314 | A1* | 10/2011 | Barker | G06F 16/93 |
| | | | | 715/255 |
| 2012/0154115 | A1* | 6/2012 | Herrala | G07C 9/28 |
| | | | | 340/5.64 |
| 2015/0154404 | A1* | 6/2015 | Patel | G06F 21/60 |
| | | | | 726/26 |
| 2015/0163206 | A1* | 6/2015 | McCarthy | H04L 63/06 |
| | | | | 713/171 |
| 2016/0352726 | A1* | 12/2016 | Hyde | H04W 12/082 |
| 2017/0228381 | A1* | 8/2017 | Nazaruk | G06F 21/6227 |

OTHER PUBLICATIONS

Cramer, R. et al., "Multiparty Computation from Threshold Homomorphic Encryption". EUROCRYPT '01 Proceedings of the International Conference on the Theory and Application of Cryptographic Techniques: Advances in Cryptology, pp. 280-299, May 6-10, 2001, UK.

* cited by examiner

LOCATION TRACKING ENABLING PRIVACY PROTECTION

FIELD OF THE INVENTION

The invention relates to location tracking system, a connected location-analysis device, an unconnected location-analysis device, a tracking device, a location-analysis method, a computer readable medium.

BACKGROUND

In recent years there is an increasing interest in indoor location tracking. This can be used, e.g., in stores to automatically guide customers to the right aisles after selecting a product on the smart phone.

In a different setting, such technology can be used in hospitals to track people or assets. This can be very useful to find back misplaced equipment. In practice this may work by equipping assets with a special tag. This tag interacts with tag readers that are placed throughout a building. When the reader sees a specific tag, it registers a log entry in a central database. The other way around, e.g., locations with tags, assets with readers, may also be used. The resulting logs of location data can be processed using data analytics algorithms.

A known system is described in US patent application US20080126126 A1, "Method And Apparatus For Managing And Locating Hospital Assets, Patients And Personnel", incorporated herein by reference. The known system discloses an apparatus and method for facilitating locating, tracking and managing of hospital assets, patients and hospital personnel within a healthcare facility, providing one or more signal detecting devices configured in locations within a healthcare facility, providing associated patient RFID tags which may be sensed as the patient moves within the range of a signal detecting device, where one or more zones of detection within the healthcare facility are configured to correspond with hospital units, and where the information may be collected and used in real-time to manage patients, assets and staff through the collection of location and dwell times, and alerting and reporting of events associated with the collected information.

Tracking every move of every employee may be regarded as an infringement of privacy. This may hamper adoption of this technology. One way of protecting such information may be to make sure that the log information is protected using administrative policies: e.g., the logs are stored on a well-protected computer, and only accessed for very specific purposes. Such policies may not offer sufficient protection though; the tracking technology, the logs and the eventual data analytics are all still under control of one party, e.g., the hospital. There are no technical guarantees that the logs will not be used for different purposes.

SUMMARY OF THE INVENTION

To address these and other concerns, a location-tracking system is proposed as defined in the claims. Location updates are stored but they are encrypted by a database encryption key. No party has unfettered access to all of the location data, and thus no party can unilaterally perform analytics on the data. On the other hand, analysis of tracking data remains possible if the parties agree that the analysis is acceptable, e.g., promotes some common goal, and/or does not infringe on certain rules, e.g., does not infringe privacy regulations.

Performing such analytics can be beneficial. For example, they may allow a hospital to identify workflow bottlenecks and optimize for them, check adherence to hospital protocol, and even, e.g., in case of an infection, determine which persons and/or rooms need to be quarantined. Similar scenarios exist outside of hospitals: in stores, factories, office buildings, etc.

Performing analysis on encrypted location updates may be done using key-shares of a cryptographic database decryption-key corresponding to the cryptographic database encryption-key. The key-shares are stored at multiple location analysis devices. The devices may be under the control of parties with opposing goals, e.g., hospital management and a controlling party such as worker's council, a union, etc. Interestingly, using the key-shares the location analysis devices may engage in a multi-party computation protocol in which location analytics may be computed, yet without infringing on privacy. Once the desired results have been obtained, although under the cloak of the multi-party computation, e.g., as a secret-shared result, only the desired value, e.g., the final location-analysis result, may be opened. The latter may be done by receiving a share in the location-analysis result and combining it with a share in the location-analysis result that is locally available as a result of the multi-party computation to the open location-analysis result. In addition, or instead, the share in the location-analysis result that is locally available may be sent to another location analysis device, so that it can open the location-analysis result. As desired, one, more or all location analysis devices may be open the location-analysis result.

An aspect of the invention concerns the location-analysis device. A location-analysis device may be connected to a location database for receiving location updates encrypted with a cryptographic database key from the location database. The connected location-analysis device may then engage in a multi-party computation protocol with one or more other location-analysis devices. The other location-analysis device may receive their information on the location updates directly from the database as well, but instead they may receive information on the location updates from a location-analysis device. The latter situation is advantageous since it allows the database to be shielded; in an embodiment it would only need to communicate with a single one of the location analysis devices. An aspect of the invention concerns unconnected location analysis devices that receive location updates from another location-analysis device as a private input to a multi-party computation.

In an embodiment, the location update comprises a class attribute. One or more, but not all of the location analysis devices are allowed plain access to location updates having one or more particular values of the class attribute. Access to the location updates is thus divided using the class attributes ensuring an improvement in privacy protection, but at the same time allowing at least part of the analysis computation to be done on plain values. For example, the multi-party computation protocol may comprise a joint decryption for the location-analysis device of location updates wherein the class attribute equals one of the one or more particular values. Location-analysis devices associated with the one or more particular values obtain the decrypted location updates. Performing a computation on decrypted location updates is much faster. Although this may result in one or more plain computation results, these may be entered back into the multi-party computation as a private input. The location-analysis result may depend on the computation result. For example, the location-analysis may be computed at least from one or more entered computation results as a multi-party computation. The result of the latter may be opened as indicated above.

Embodiments address privacy concerns that occur when performing location tracking. We propose a way to perform privacy preserving analysis of location tracking logs.

The location analysis devices may be electronic devices. For example, they may be a computer.

An aspect of the invention concerns a tracking device for use in a location tracking system. For example, the tracking device may comprise a key storage for storing the database encryption-key, and an encryption unit configured to encrypt the location updates with the database encryption-key. For example, the database encryption-key may be an encryption key according to a threshold homomorphic encryption scheme.

An aspect of the invention concerns location analysis methods. Such methods may be applied in a wide range of practical applications. Such practical applications include the analysis of logistics inside or outside of buildings, offices, hospitals, and the like.

An embodiment of the method may be implemented on a computer as a computer implemented method, or in dedicated hardware, or in a combination of both. Executable code for an embodiment of the method may be stored on a computer program product. Examples of computer program products include memory devices, optical storage devices, integrated circuits, servers, online software, etc. Preferably, the computer program product comprises non-transitory program code stored on a computer readable medium for performing an embodiment of the method when said program product is executed on a computer.

In an embodiment, the computer program comprises computer program code adapted to perform all or part of the steps of an embodiment of the method when the computer program is run on a computer. Preferably, the computer program is embodied on a computer readable medium. Another aspect of the invention provides a method of making the computer program available for downloading.

BRIEF DESCRIPTION OF THE DRAWINGS

Further details, aspects, and embodiments of the invention will be described, by way of example only, with reference to the drawings. Elements in the figures are illustrated for simplicity and clarity and have not necessarily been drawn to scale. In the Figures, elements which correspond to elements already described may have the same reference numerals. In the drawings, FIG. 1 schematically shows an example of an embodiment of a location-tracking system, FIG. 2a schematically shows an example of an embodiment of a location analysis device, FIG. 2b schematically shows an example of an embodiment of a cryptographic database decryption-key and corresponding key-shares, FIG. 3 schematically shows an example of an embodiment of a location-tracking system, FIG. 4 schematically shows an example of an embodiment of a location-tracking system, FIG. 5 schematically shows an example of an embodiment of a location-tracking system, FIG. 6a schematically shows an example of an embodiment of a location analysis method, FIG. 6b schematically shows an example of an embodiment of a location analysis method, FIG. 7a schematically shows a computer readable medium having a writable part comprising a computer program according to an embodiment, FIG. 7b schematically shows a representation of a processor system according to an embodiment.

LIST OF REFERENCE NUMERALS, IN FIGS. 1-5, 7a-7b 100 a location-tracking system
110 a location data gathering subsystem
112-113 a tracking device
120 a location database
130 a cryptographic database encryption-key
140 a cryptographic database decryption-key
141-142 a key-share of the cryptographic database decryption-key
150 a computer network
151 an authorization input
200 a multi-party computation subsystem
201-202 a location analysis device
213 a communication interface
214 a memory
215 a processor
216 a key storage
221-222 a location analysis device
231-232 a location analysis device
241-243 a location analysis device
1000 a computer readable medium
1010 a writable part
1020 a computer program
1100 a device
1110 a system bus
1120 a processor
1130 a memory
1140 a user interface
1150 a communication interface
1160 a storage
1161 an operating system
1162, 1163, 1164 instructions

DETAILED DESCRIPTION OF EMBODIMENTS

Figure 1:
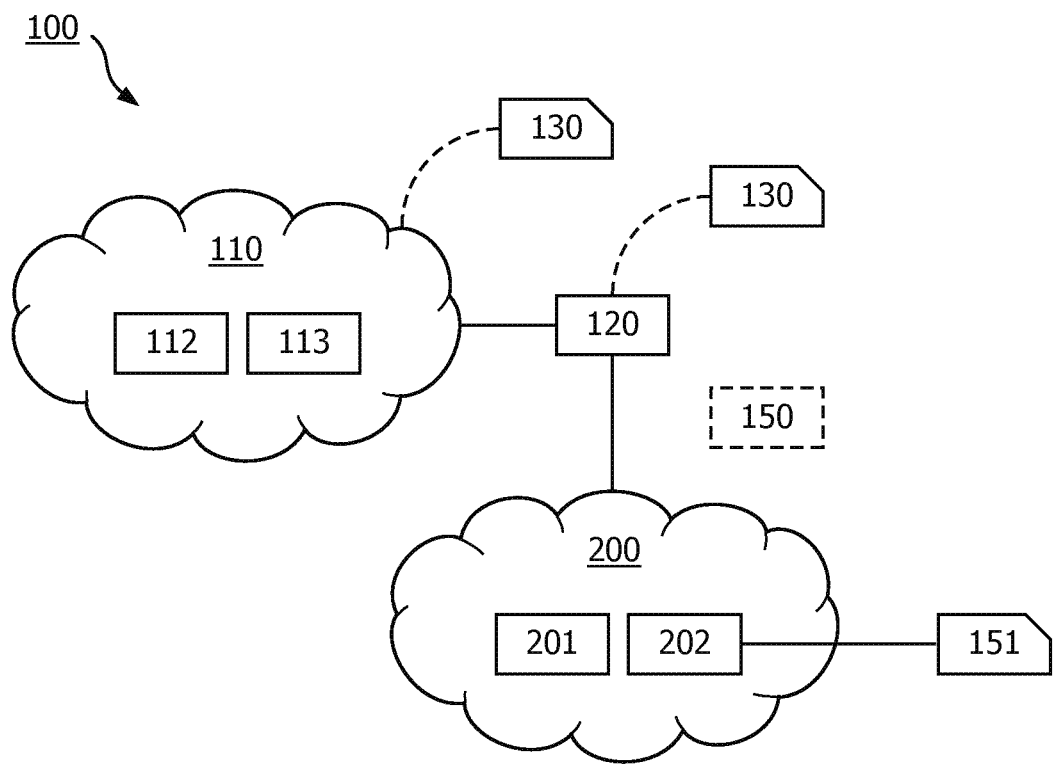

While this invention is susceptible of embodiment in many different forms, there are shown in the drawings and will herein be described in detail one or more specific embodiments, with the understanding that the present disclosure is to be considered as exemplary of the principles of the invention and not intended to limit the invention to the specific embodiments shown and described.

In the following, for the sake of understanding, elements of embodiments are described in operation. However, it will be apparent that the respective elements are arranged to perform the functions being described as performed by them.

Further, the invention is not limited to the embodiments, and the invention lies in each and every novel feature or combination of features described herein or recited in mutually different dependent claims.

FIG. 1 schematically shows an example of an embodiment of a location-tracking system 100. System 100 comprises a location data gathering subsystem 110, a location database 120, and a multi-party computation subsystem 200.

The location data gathering subsystem 110 may comprise a plurality of tracking devices configured to track one or more objects, e.g., assets, e.g., live or non-live assets, e.g., humans, animals, and material objects, e.g., non-living objects, e.g., beds, stretchers, etc. For example, in an embodiment, the plurality of tracking devices may comprise a reader arranged to detect the presence and absence of tags in an area surrounding the reader, said readers being configured to send a digital signal to enable storage of the encrypted location updates. For example, the tags may be RFID tags. For example, the plurality of tracking devices may be installed at fixed locations, and the tags are affixed to the one or more objects. For example, the plurality of tracking devices may be affixed to the one or more objects, and the tags are installed at fixed locations. Various solutions for tracking objects that are known in the literature may be employed in an embodiment.

In an embodiment, lamps emit an identifier in visible light (VLC) that indicates the location of the lamps. A tracking device, e.g., a mobile phone may be configured to receive the identifier. This indicates that the tracking device is in the vicinity of the lamp, and thus in the vicinity of the indicated location. Identifiers may be transmitted in other wireless forms as well, e.g., in the form of radio signals.

In addition to radio waves (RF) and visible light coding, there are several other options for location tracking, and in particular, in door location tracking. For example, an advantageous location tracking system uses infrared (IR); for example, see U.S. Pat. No. 8,139,945B1. The system includes an apparatus for transmitting timing synchronization information, a plurality of stationary infrared (IR) base stations and a plurality of portable devices. Each IR base station is configured to receive the timing synchronization information and to transmit a corresponding IR location code in a time period based on the received timing synchronization information. Each portable device is configured to: 1) receive the timing synchronization information, 2) detect the IR location codes from the IR base stations and 3) transmit an output signal including a portable device ID representative of the portable device and the detected IR location code. Each portable device is synchronized to detect the IR location code in the time period based on the received timing synchronization information. Another option is to use ultrasound based systems for location tracking, see, e.g., US20050141345A1. In yet a further embodiment, individuals may be tracked though the wireless signals that bounce off them. These wireless signals are transmitted by a normal WiFi base station. The base station then measures the reflections and uses algorithms to track an individual. In this case, the individual does not need to wear any tags; see, e.g., "SpotFi: Decimeter Level Localization Using WiFi", by M. Kotaru, et al.

A tracking device, especially a mobile tracking device, may receive identifiers from multiple sources and derive an improved location therefrom with increased accuracy, e.g., by using triangulation. In an embodiment, the identifier may indicate a room number, or a part of a room, etc. FIG. 1 shows two tracking devices: tracking device 112 and tracking device 113; there may be more than 2, e.g., more than 10, more than 100, more than 1000, etc.

The location gathering subsystem 110 may be configured to send location updates from the tracking devices to database 120. For example, a tracking device may comprise a communication interface to connect to database 120, e.g., through a digital network. The connection may employ one or more intermediaries, e.g., routers, buffers, and the like. A location update may comprise one or more of the following information: a timestamp, a location, an identifier of the object. For example, the timestamp may indicate when the object was located at the location. The location may comprise coordinates, or a room number, or a reader identifier, etc. The object identifier may identify, e.g., a particular person, e.g., an employee, a patient, etc. The object identifier may identifier a particular class of persons, e.g., the class employees, the class doctors, the class patients, and so on. The object may be a material object, e.g., a bed.

As a motivating example, the location gathering subsystem 110 may be a hospital in which people, say patients and employees, are tracked. For example, the people may be provided with a tag and/or a tracking device. Using the location updates various statistics about the hospital may be computed, e.g., room utilization, e.g., patients per room per hour, employee utilization, e.g., employee per room per hour, employee to patient ratio, e.g., employees per patients per room, e.g., per hour, and so on. Such detailed location information has a privacy risk though. In addition to computing system metrics, in which location information of multiple different objects are aggregated, the location updates could also be used to obtain information on the whereabouts of individual employees or patients. Embodiments can avoid deriving information that is unwanted, e.g., because of privacy concerns, while at the same time allowing deriving information that is desirable, e.g., computing metrics that involve multiple persons, etc.

In an embodiment, location database 120 is configured to store the plurality of location updates encrypted with a cryptographic database encryption-key 130. The encryption may be done in multiple ways. For example, in an embodiment, one or more or all of the tracking devices may comprise a key storage storing database encryption-key 130. The tracking device may encrypt the location update before sending it to the location update. For example, the tracking device may be configured by some party, e.g., the manufacturer, with database encryption-key 130. This option is illustrated in FIG. 1, by a dashed line between key 130 and subsystem 110. Another option is to encrypt the location updates in location database 120. For example, location database 120 may comprise a key storage storing database encryption-key 130. For example, location updates may be received in plain from tracking devices and encrypted before storing by database 120. The latter is illustrated as a dashed line between database 120 and key 130. Hybrids are possible, e.g., part of the location updates may be encrypted in subsystem 110 and part in database 120.

Database encryption-key 130 may be a public key, e.g., knowledge of database encryption-key 130 does not give information for decrypting location updates that were encrypted with database encryption-key 130. For example, database encryption-key 130 may be a Paillier public key or an ElGamal public key; both options support threshold homomorphic cryptography. In another example, database key 130 may be a symmetric key. For example, database key 130 may be block cipher key, e.g., an AES key. As will be described herein, in an embodiment the database key 130 may comprise multiple symmetric subkeys $K=(K_1, K_2, \ldots)$. In this case, encryption may be concatenated encryption with each of the subkeys, e.g., $E_{K_1} \circ E_2 \circ \ldots$; for example, addition of multiple stream ciphers, e.g., in which a pseudorandom stream is computed from a subkey.

A database decryption key 140 corresponds to the database encryption key 130. In case of asymmetric encryption, knowledge of the encryption key 130 may not reveal information on the decryption key 140. In case of symmetric keys, the encryption key 130 and decryption key 140 may be equivalent, e.g., one may be computed from the other, or they may even be the same. Decryption key 140 is only provided to trusted parties, e.g., parties that are trusted not to compute or reveal sensitive information, e.g., privacy information. Interestingly, without knowledge of the decryption key 140, the value of the encrypted information in the database 120 is small or even de-minimis.

To compute useful information from the encrypted information stored in database 120, system 100 comprises multiple location-analysis devices, in this case organized in a multi-party computation sub-system 200. Shown are location analysis device 201 and location analysis device 202. There are at least two location analysis devices, but there may be more than 2, more than 3, etc.

Figure 2A:
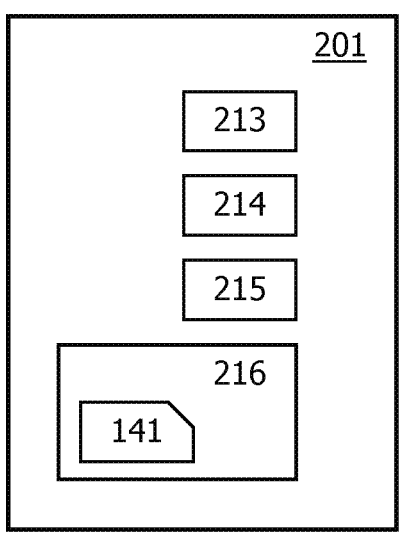

FIG. 2a schematically shows an example of an embodiment of a location analysis device in more detail, in this case location analysis device 201. The other location analysis devices may have the same or a similar design. Location analysis device 201 may comprise a communication interface 213, a memory 214, a processor 215, and a key storage 216.

Communication interface 213 is arranged to communicate with at least one other location-analysis device of the multiple location-analysis devices, allowing the multiple location analysis devices to jointly execute a multi-party computation protocol. Communication interface 213 is also configured to obtain location updates from database 120. This may be directly, e.g., communication interface 213 may be configured to receive location updates encrypted with the cryptographic database key from location database 120. In this case we refer to the location analysis device as 'connected'. The location analysis device may also receive location updates from a different source, e.g., indirectly via another location analysis device. In the latter case we refer to the location analysis device as 'unconnected'. For example, an unconnected location analysis device may receive the location updates encrypted with the database encryption key 130, just as a connected device, but via a location analysis device. For example, an unconnected analysis device may receive location updates after some computation has been done on it by another location analysis device, e.g., in the form of a private input to the multi-party computation. The adjectives 'connected' and 'unconnected' in reference to a location analysis device only indicate the source from which the device receives location updates. In particular, both a connected and an unconnected device may be connected to a digital network, e.g., a computer network.

Figure 2B:
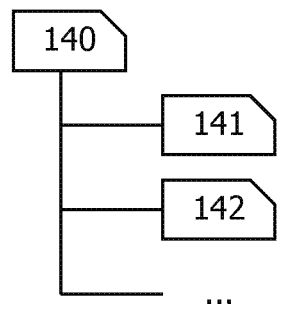

Key storage 216 is configured to store a key-share 141 of the database decryption-key 140 that corresponds to the database encryption-key 130. The cryptographic database decryption-key 140 is shared into multiple key-shares stored at the multiple location-analysis devices. FIG. 2b schematically shows an example of an embodiment of a cryptographic database decryption-key 140 and corresponding key-shares. Shown are key-share 141 and key-share 142. There may be more key-shares. For example, in an embodiment, the database encryption-key 130 and the key-shares 141, 142, of the database decryption-key 140 may be according to a threshold homomorphic encryption scheme. The threshold may refer to the number of shares that are needed to open a value. The threshold may be 2. For example, in an embodiment the database decryption-key 140 might be reconstructed from two key-shares 141 and 142. The threshold may be higher. For example, in case key 130 is a Paillier or ElGamal public key for threshold homomorphic encryption schemes, the key shares 141, and 142 may be the corresponding key-shares according to the respective threshold encryption schemes. For example, if database encryption is concatenated encryption with multiple symmetric subkeys, then the key-shares may be the subkeys. In principle the sub-keys could be any set of keys from which the database decryption key may be computed without revealing information in a too small subset of the sub-keys, e.g., the XOR of the sub-keys may be the database decryption key. In this case the database decryption key may be computed in the multi-party computation and used as a secret-shared value. This has the advantage of supporting a large variety of encryption schemes, whether symmetric or asymmetric, but it may have the downside of incurring a performance penalty.

The various devices of system 100, 110, 120 and/or 200 may communicate with each other over a computer network 150, schematically illustrated as a dashed box. The computer network may be an internet, an intranet, a LAN, a WLAN, etc. Computer network 150 may be the Internet. The computer network may be wholly or partly wired, and/or wholly or partly wireless. For example, the computer network may comprise Ethernet connections. For example, the computer network may comprise wireless connections, such as Wi-Fi, ZigBee, and the like. The devices comprise a connection interface which is arranged to communicate with other devices of the system as needed. For example, the connection interface may comprise a connector, e.g., a wired connector, e.g., an Ethernet connector, an optical connector, etc., or a wireless connector, e.g., an antenna, e.g., a Wi-Fi, 4G or 5G antenna. For example, the location analysis devices, tracking devices and/or database 120 may comprise communication interfaces, e.g., communication interface 213. Computer network 150 may comprise additional elements, e.g., a router, a hub, etc. In device 201, the communication interface 213 may be used to receive location updates and to exchange messages of a multi-party computation (mpc). The messages may be digital messages, e.g., received in electronic form.

The execution of the system and methods may be implemented in a processor circuit, examples of which are shown herein. For example, functional units, such as a communication unit or an mpc unit, e.g., of a location analysis device may be wholly or partially implemented in computer instructions that are stored at a location analysis device, e.g., in an electronic memory 214 of device 201, and are executable by a microprocessor of the device, e.g., processor 215 of device 201. In hybrid embodiments, functional units are implemented partially in hardware, e.g., as coprocessors, e.g., crypto coprocessors, and partially in software stored and executed on a location analysis device, e.g., device 201.

Returning to FIG. 1. The location analysis devices, e.g., their processors, are configured to execute a multi-party computation protocol among the multiple location-analysis devices on the encrypted location updates using the stored key-share, thus jointly computing a location-analysis result secret-shared among the multiple location analysis devices. A multi-party computation is sometimes referred to as a secure multi-party computation, secure computation, multi-party computation/MPC, or privacy-preserving computation. In an mpc, the parties may jointly perform a computation without the parties learning more about information of the other parties than what can be derived from the final computation result. For example, in an embodiment, the parties, in this case the location analysis devices, receive location updates that are fully or partially encrypted. Although a location analysis device could gain access to the plain location updates if it had access to the other key-shares, the mpc is configured so that a location analysis device does not obtain these. In other words, a location analysis device does not have sufficient information to decrypt the location updates to begin with, and does not learn additional information that would enable him to decrypt the location updates after the mpc has completed. A partial decrypted location update may be an encrypted location update which has been decrypted for a key-share, rather than for the full decryption key. Typically, decryption by a key-share is not sufficient to obtain plain information. For example, in the context of a threshold encryption scheme, a partial decrypted location update requires fewer additional key-shares than the original threshold for decryption.

The outcome of the mpc may be a location-analysis result that is secret-shared among the parties. This means that the parties do not yet have access to the plain location-analysis result. However, by combining multiple shares in the location-analysis, the secret-shared location-analysis result may be opened. For example, the location analysis devices may be configured to each send a share in the location-analysis result to all other location analysis device so that each can open the location-analysis result. For example, all-but-one location analysis device may send a share in the location-analysis result to one particular location analysis device who can then open the location-analysis result. Various other combinations are possible.

The multi-party computation may be based on a threshold homomorphic encryption scheme, in which case the location analysis devices can perform operations on the encrypted location updates with their key-shares. In such an embodiment, all intermediate results and the final location-analysis result may be encrypted with the database encryption key. A value that requires the cooperation of multiple parties, e.g., multiple location analysis devices, to obtain the corresponding plain value may be regarded as secret-shared. For example, values that are encrypted with the database encryption key may be regarded as secret-shared values of the threshold homomorphic encryption schemes. Alternatively, the location updates are decrypted in the multi-party computation but secret-shares. This means that they are no longer encrypted with the database encryption key, although the parties still cannot access the location updates in the plain, since the decryption is done as an mpc, resulting in secret-shared decrypted location updates. The latter has the advantage that mpc schemes may be used that are not necessarily based on threshold homomorphic encryption. Suitable mpc schemes include Shamir secret sharing and additive secret sharing, e.g., as implemented using the SPDZ protocol, see, e.g., "Practical Covertly Secure MPC for Dishonest Majority—or: Breaking the SPDZ Limits", by Damgård, et al.

For example, the mpc protocol may be configured to count location updates at or near an input-location; For example, location updates in particular locations or at particular times and so on. The input-location may be hard-wired in the mpc, or may be a private input of one of the parties. One way in which this can be done is by performing multiple oblivious comparisons between an encrypted location update and the input-location. In other words, the oblivious comparison may compare the location in a secret-shared location update with the input-location, without revealing if the comparison was successful or not, and in particular without revealing information on the location update or its content. Accordingly, an architecture has been defined that allows storing of tracking data logs and allows performing a multi-party computation. For example, the mpc protocol may comprise oblivious comparison of encrypted timeslots, comparisons on whether log entries belong to the same person, and comparison of attributes in the location update with given attributes, e.g., class attributes.

Returning to the motivating example, regarding hospital patient and employee data. An embodiment may be used, e.g., to split parties by incentive. For example into two parties: a first party, which we may call the management party, and a second party, which we may call the controlling party. For example, the controlling party may be a worker's council, a union, an ombudsman, etc.

The management party may control the physical location where tracking takes place. The management has an interest in getting as much tracking data as possible, as it has the potential to improve their business. In this example, this may be the management of a hospital. It could also be a store, a factory, etc. The management may buy the tracking hardware, e.g., from a manufacturer and install it on premise. Once in use, the tracking devices store the generated and encrypted tracking logs in a database. The database may be considered to be completely under control of the management, though possibly located in the cloud.

The controlling party may protect the interest of employees under the employ of the management above. It is their job to make sure that tracking information is only used for very specific purposes, and preserve the privacy of the employees. In our example this may be a controlling party at the hospital, but it could also be a representative of a union, etc. In other scenarios it could be a consumer organization, or a privacy watchdog, and so on.

The controlling party controls a computation server or computation cloud that is outside the control of the management. This server also takes part in multi-party computations on the tracking logs.

In an embodiment, the motivating example may work as follows. A manufacturer creates tags and tag readers. The manufacturer may adapt its readers in such a way that it only outputs encrypted logs. We assume that the manufacturer is a trusted third party. That means: the readers may only output encrypted tracking logs, and the management has no other way of getting to these logs than through processing of the encrypted data. Other options are possible, as discussed herein. The tags and readers may be programmed by a trusted party other than the manufacturer.

Set up may be done as follows:

i. Management buys and install tag readers from manufacturer, sets up database for tracking logs.

ii. Management and controlling party agree on the type of computations that can be done.

iii. Management sets up a management computation computer, e.g., cloud server. As part of this step, key material may be generated.

iv. The controlling party sets up a control computation computer, e.g., cloud server. As part of this step, key material may be generated. For example, the controlling party computer and the management computer may jointly compute the database encryption key.

v. Management programs the generated key material into the reader.

vi. Management distributes tags to employees and optionally assets, etc.

Tracking may be done as follows:

i. If a reader sees a tag, the reader may determine location information, time information and object information. For example, the reader may determine one or more of the following information: tag-number, room number, timestamp ii. The reader uses the key material to encrypt these items in such a way that management and controlling party must work together to decrypt the data, e.g., using a threshold encryption. There are several methods by which this can be done.

Location analysis may be done as follows:

i. The management computation server reads the encrypted log data from the database ii. The management computation server initiates a multi-party computation iii. In response, the controlling party computation server reads the encrypted log data from the database.

iv. The two servers together initiate a multi-party protocol that uses these encrypted logs as input.

Interestingly, this process works for any multi-party computation. Furthermore, since the tracking log database only contains encrypted data, it could in fact be (semi-)publicly accessible. This may even be a good thing, as it can clearly show employees that there is no privacy infringement. This example can be extended to more parties. An example would be: management, a controlling party (e.g., for employees), a patient organization (for patients). Another example would be multiple collocated businesses in a single building, with multiple managements and multiple controlling parties.

The architecture as described assumes that management is interested in the results of the analytics, and the controlling party joins in the computation to protect privacy. However, the same architecture may be used in cases where the controlling party is interested in information or where both parties are interested in the output.

In an embodiment, the controlling party's computation computer may passively respond to an initiated computation. This means that only a set of predetermined computations can be performed, and at any time the management wants. There are several ways to change this. For example, as a safety measure, the controlling party's computation server may require authorization before running. This authorization may be performed by a representative of the controlling party. For example, the controlling party computation server may send a message to the representative, e.g., via e-mail or a mobile app, etc. The representative is then required to confirm the start of the computation before the server will actually start computing.

A second approach may be where the controlling party computation computer will already perform the whole privacy preserving computation (multi-party computation), but withholds the last step of opening the results. This is possible, since the computation server already has or can acquire all information needed to perform the computation. The results of the computation will only be disclosed after authorization, as in the previous paragraph. An advantage of this approach is that the representative remains in control, yet no time is lost in performing the multi-party computation, e.g., between the management computer and the controlling computer.

A third approach allows management to propose a different computation from the ones already agreed on. The representative reviews the computation and authorizes it before the computation server will participate in the multi-party computation of this computation.

Note, that a logical fourth approach might be to combine 3 with the ahead-of-authorization computation of 2. However, an unauthorized computation could already reveal information during its computation. It is thus advisable that new computations are thoroughly checked before they are allowed to run.

For example, in the context of FIG. 1, optionally, one of the location analysis devices may require an authorization input 151. The authorization may be cryptographically protected, e.g., it may comprise a digital signature. Note that the authorization input 151 does not need to be part of the mpc. In an embodiment, none, one or more, or all localization analysis devices require an authorization input before starting the computation and/or before revealing the localization analysis result. For example, in an embodiment, the communication interface may be arranged to receive the authorization input. The processor may be configured to allow execution of the multi-party computation protocol before receiving the authorization input and to require receiving the authorization input before computing or sending the share in the decrypted location-analysis result for opening the encrypted location-analysis result. For example, authorization input 151 may comprise an authentication token, e.g., a digital signature or a mac, etc., from an authorized person. Device 202 may verify the authentication token before enabling opening of the analysis result, etc.

Returning to the FIG. 1. As pointed out above, using multi-party computations, e.g., using multiple oblivious comparisons, any computation that is desired to be performed on the data, and any computation that all parties can agree to may be performed without revealing any additional data than would be contained in the final analysis result. Although such a computation would be significantly slower than analysis on plain data, this would nonetheless be feasible. However, the inventors realized that an optimization is possible which speeds up the mpc computation to levels that may be very nearly to the same speed as the plain computation. The motivating example above reveals that not all parties are trusted or mis-trusted equally with respect to all localization information. For example, hospital management may be trusted with patient localization data, but not with employee localization data. Likewise, a controlling party, like a worker's council, may not be trusted with patient localization data, but would be trusted for employee localization data. It was an insight of the inventors that large parts of typical localization related computations are performed on data of the same class, e.g., only on patient data, or only on employee data.

In an embodiment, a location update comprises a class attribute. For example, a class attribute may be obtained from a reader or tag ID. For example, a look-up table may associate reader or tag IDs with a class attribute. For example, a class attribute may be comprised in a reader or tag ID and obtained by a tracking device. For example, the class attribute may be included in the location update by the tracking device. In the latter case no look-up table is needed. If a look-up table is used, this may be done by database 120, e.g., before encrypting the location update.

One or more of the location-analysis devices may be associated with one or more particular values of the class attribute. For example, a class attribute may indicate the type of object that is tracked. For example, a class attribute may indicate if the location update relates to a person or a material object, or the type of person, or the type of object, etc. In an embodiment, the class attribute is binary; one class value being associated with a first location analysis device and other class value being associated with a second location analysis device. For example, referring to the motivating example, the class attribute may indicate if the location update relates to a patient or to an employee.

The multi-party computation protocol comprises joint decryption for the location-analysis device of location updates wherein the class attribute equals one of the one or more particular values, wherein location-analysis devices associated with the one or more particular values obtain the decrypted location updates.

For example, the location analysis devices may partially decrypt a location update associated to a particular class attribute for their key-share, and then send the partially decrypted location update to the location analysis device that is associated with that particular class attribute. The receiving location analysis device that is associated with that particular class attribute then combines the partial decryptions to obtain a fully decrypted location update. Only the location analysis device that is associated with the particular class value gains access to the plain location updates. This option is for example efficient with threshold encryption schemes such as Paillier and ElGamal.

Another way to achieve this may be to fully decrypt the location updates as a multi-party computation joint with the other location analysis devices. In this case, the result may be a fully decrypted location update but secret-shared among the location analysis devices. After that, the location analysis devices may send a share in the fully decrypted location update to the location analysis device that is associated with the particular class value. For example, the multi-party computation may start with computing a secret-shared decryption key, or with partial decryption and secret-sharing of decryption information.

The end result of either mechanism is that the location analysis device that is associated with the particular class value obtains the location updates that are associated with the particular class value. One location analysis device may be associated with multiple class values; for example, the class attribute may indicate doctors and nurses, both of which may be handled by the same location analysis device. Likewise, multiple location analysis devices may be associated with the same or overlapping class attributes. However, location analysis devices are not associated with multiple class attributes if having access to the corresponding plain location updates would imply privacy concerns. For example, preferably, a location analysis device would not be associated with both the patient and employee class.

Having access to part of the location updates in plain implies a level of privacy, since none of the location analysis devices gains access to all location updates, but also improves efficiency. Any part of the computation that only involves the location updates for a particular class can be done in plain, which is much faster. For example, the multi-party protocol may comprise performing a computation by the location-analysis device associated with the one or more particular values on the decrypted location updates that comprise the one or more particular class attribute values, obtaining a plain computation result. After this computation, the computation result may be entered into the multi-party computation as a private input. For example, the result may be secret-shared, e.g., the result may be encrypted with a public database encryption key, or an additive or multiplicative share such as in SPDZ or Shamir secret sharing. The multi-party computation then computes the location-analysis result from at least the computation result.

For example, in case a patient to employee ratio for a particular area and a particular time interval is required. One may have one location analysis device associated with the class attribute patient, and one other location analysis device associated with the class attribute employee. The multi-party computation then identifies the location updates that have the class attribute patient and arranges the decryption of these location updates to be obtained by the location analysis device associated with the patient class attribute. Likewise, the multi-party computation identifiers the location updates that have the class attribute employee and arranges the decryption of these location updates to be obtained by the location analysis device associated with the employee class attribute. The location analysis devices can then count the location updates for the correct locations and times. The location analysis devices may also easily verify that the location updates correspond to unique objects, etc. The resulting counts may then be entered as private inputs. Under the cloak of the multi-party computation the ratio between these may then be computed and opened.

In an embodiment, the class attributes are not encrypted and available in plain as part of a location update, or associated with a location update. For example, the location database 120 could store the class attribute in plain next to an encrypted location update, etc. Alternatively, the class attribute may be encrypted, in that case, the class attribute may be decrypted in the multi-party computation. The resulting decrypted class attribute can then be opened, on all location analysis devices, e.g., as indicated above for location updates. The location analysis devices can then proceed to decrypt the correct location updates for the correct location analysis devices. In an embodiment, the class attribute is encrypted in database 120 such that the decryption key is available to all location analysis devices; the encryption and decryption key may be symmetric or asymmetric. This does not change the privacy level if the class attribute would become available in plain to the devices anyway, but does protect the class attribute while it is stored in the database.

Instead of comprising the class attributes directly the location updates may comprise an encrypted ID of the tracked object. In this case the identifier may be mapped to a class attribute in the multi-party computation, and the resulting class attribute may then be opened for the location analysis devices.

For example, in an embodiment the class attributes may be encrypted with the database encryption-key, the multi-party computation protocol comprising a joint decryption of the class attribute by the multiple location-analysis devices, e.g., using the key-shares. The latter may result in a secret-shared class attribute, which in turn may be opened for the location analysis device, e.g., all of them.

Although the class attributes reveal little information, there may be a concern that information contained therein needs to be reduced. In an embodiment, the location updates comprise dummy location updates for at least some of the one or more particular values of the class attribute. For example, a location update may comprise if it is a dummy update or not. The latter information is encrypted and only available to the location analysis devices that have access to the plain location updates. The processor may be configured to discard the dummy location updates after obtaining the decrypted location updates.

For example, a tracking device may generate dummy location updates, e.g., in addition to its regular location updates. For example, the tracking device may send a percentage of the location updates as dummy updates. For example, the dummy updates may be generated by the location database 120. For example, a location update may have a random class attribute. After encryption with the database encryption key, the update is indistinguishable from a regular update. In this way, the class attribute may be plain. This solution incurs a cost for additional decryptions, but on the other hand avoids the cost of doing the full computation as a multi-party computation. For example, a predetermined percentage of the location updates may be a dummy location update; e.g., the percentage may be 10% or more or less, etc. A dummy update may comprise a unique salt. Dummy updates may have a class attribute which may be random; they may be chosen from a probability distribution. For example, the distribution of dummy classes may be approximately equal to the distribution of the classes in real location updates. The probability distribution may be pre-determined. In an embodiment, the probability distribution is jointly computed using an mpc according to an embodiment.

A potential drawback of performing part of the analysis on plain data is that the resulting system is less resistant against active attacks from non-honest location analysis devices. For example, the location analysis device with access to patient data could illegally increase or decrease the count of patients and thus illegally increase or decrease the patient to employee ratio. Likewise, for the location analysis device that has access to plain employee location data. Resistance against active attacks is not necessarily a requirement for multi-party computations. After all, the corresponding non multi-party computation is not resistant to active attacks either, in addition to having privacy concerns. In an embodiment, at least one further location-analysis device is associated with the one or more particular values of the class attribute. For example, at least two different analysis location devices may be associated with a class attribute value, or even with each class attribute value. For example, in an embodiment, for each class attribute value at least two location analysis devices are associated, but each location analysis device is associated with only one class attribute.

An advantage of having multiple location analysis devices associated with the same class attribute values is that the computations on the decrypted location updates can be performed as well in the multiple associated location analysis devices. For example, each of the multiple location analysis devices associated with the same class attribute values obtains the corresponding plain location updates. As a result, the multiple location analysis devices associated with the same class attribute values compute multiple plain computation results. The multiple plain computation results may then all be entered as private inputs into the multi-party computation At this point, the multi-party computation may comprise a verification step in which the secret-shared multiple computation results are compared for equality; note that this step does not reveal any additional information to the parties than whether the plain multiple computation results were equal or not. For example, the multiple computation results could be multiple counts of employees in one or more particular locations during some time-interval. If the values are not equal, the computation may be aborted. If the values are equal, the computation may be continued, e.g., by performing an mpc division with one of the multiple computation results and some other value, and so on. For example, a secret-share comparison result may first be computed as an mpc, which may be then be opened to all parties, so that each party can verify if the computation is to be continued.

However, an alternative approach avoids having to perform an equality test within the multi-party computation. For example, after entering the multiple computation results into the multi-party computation by sharing the computation results with one or more location-analysis devices, the multi-party computation may proceed as usual but is repeated for each one of the multiple computation results. As a result, the multi-party computation obtains multiple secret-shared location-analysis results, each one of the multiple location-analysis results depending on a respective one of the multiple computation results. These multiple secret-shared location-analysis results can then be opened, e.g., by sending partial decryptions or sending shares in the multiple secret-shared location-analysis results. The opened location-analysis can then be compared for equality in the plain.

Avoiding the comparison as an mpc is particularly advantageous if the location analysis devices that have plain access to the location updates of a particular class or classes do not joint in the same mpc protocol. Typically, all of the location analysis devices join in the same mpc. Although a different mpc may be used to decrypt location updates, and to compute the computation results, typically, multiple mpc's do not run in parallel. However, splitting up part of the mpc can be advantageous. For example, in an embodiment at least one further location-analysis device is associated with the one or more particular values of the class attribute. As an example, call these devices A1 and A2. For example, A1 and A2 may be devices having access to patient records. Call another device B. For example, B may be a device that has plain access to employee records. The computation is performed by the multiple location-analysis devices associated with the one or more particular values on the decrypted location updates, obtaining multiple plain computation results. For example, both A1 and A2 receive plain access to location updates and both count patient totals, e.g., number of distinct patients in an area in some time interval, etc. There may be multiple totals. Device B may compute a total on different location updates. For example, B may compute one or more employee counts.

In an embodiment, the location-analysis devices are configured for entering the multiple computation results into multiple multi-party computations by sharing the computation results with one or more location-analysis devices. For example, the devices A1 and A2 each join into an mpc computation with B; however these mpc computations are distinct. Values of one mpc computations are not compatible with the other. A value cannot easily be transferred from one computation to the other. Note that pair A1 and B, as well as pair A2 and B may already be engaged in respective mpc computations to decrypt location updates; this is not necessary though. Decryption the location updates may be a distinct mpc. For example, all devices, say $\{A1, A2, B\}$ may jointly decrypt location updates in a first mpc, after which the devices perform their plain counts. Next $\{A1, B\}$ and $\{A2, B\}$ each join in an mpc to compute the results, e.g., the desired metrics. Multiple secret-shared location-analysis results may be obtained from the multiple multi-party computations, each one of the multiple location-analysis results depending on a respective one of the multiple computation results. For example, the mpc between $\{A1, B\}$ and $\{A2, B\}$ may each produce a computation result. Comparing these result in the mpc is difficult since they are in distinct mpc's, but comparing the final result in the plain is straightforward. For example, the devices may open the multiple secret-shared location-analysis results and compare the equality of the multiple opened location-analysis results. If at most one of A1 and A2 produces an incorrect count, then this will later be detected. Note that mpc computation on fewer devices requires less overhead then mpc over more devices. In particular, mpc on two devices is easier than over three devices. The example above may be extended, e.g., to multiple device A1, A2, A3, . . . , and/or to multiple devices B1, B2, etc. For example, the mpc's may be computed in pairs, e.g., as $\{A1, B1\}, \{A2, B2\}, \{A3, B2\}$.

In an embodiment, the location analysis device may count location updates at or near an input-location of location updates comprising one or more particular class attributes, the counting being done on plain location updates. The count may be restricted in various ways, e.g., to a particular time interval, a particular location, a particular area around the location, etc. After computing the count, and entering it as a private input into the multi-party computation, a computation may be performed on it, e.g., a multi-party division on two or more secret-shared values obtained from counting plain location updates. The resulting division may be opened, but could also be used for further computations.

For example, in an embodiment a first location analysis computes counts $p_i$, wherein i runs over multiple locations or areas, e.g., over multiple rooms. For example, $p_i$ may represent a patient count in some time interval, or over all the data, etc. A second location analysis computes counts $e_i$, wherein i runs over the same multiple locations or areas. For example, $e_i$ may represent an employee patient count in some time interval, or over all the data, etc. The values $p_i$ and $e_i$ may be computed from plain data, but on different location analysis devices and then entered back into the multi-party computation as secret-shared data; for example, the first location analysis device may compute two shares for each $p_i$ and send one to the other device and keep the other share, and the second location analysis may compute two shares for each $e_i$ and send one to the other device and keep the other. In the mpc, the ratios $p_i/e_i$ may be computed as secret-shares and may be, say, averaged. For example they may compute $1/n\ \Sigma(p_i/e_i)$, wherein n the number of areas over which the summation is performed, and wherein the values $p_i$ and $e_i$ are secret-shared values. The resulting average gives valuable information, e.g., the average patient to employee ratio, but without revealing the values $p_i$ and $e_i$ to both parties.

As described herein, the tracking technology may be used to track several classes of things. In our motivating example, this may be: employees, patients, and possibly assets. These classes all have different privacy requirements. Although generic multi-party computations may be inefficient, using the difference in classes may be used to optimize multi-party computations by selective decryption. For example, in the case where a hospital tracks both employees and patients. Location tracking of employees may be privacy sensitive and preferred to be hidden from hospital management. However, it could be revealed to the controlling party, e.g., to a work council. Similarly, the location of patients may not be secret to hospital management, but the controlling party has no need to see this information. Some classes may even be decrypted for all location analysis devices, e.g., some asset classes.

In an embodiment, tags reveal the class to the reader. The reader includes the class into the log entry, but does not encrypt it. The two computation servers may perform a specific multi-party computation. In this computation they may go through each tracking log entry. If the class is 'employee', the computation ensures sure that the controlling party's computation server will get a decryption of the entry, but not management. If the class is 'patient', the computation makes sure that the management computation server will get a decryption of the entry, but not the controlling party.

The two computation servers perform the actual computation. This computation can be a lot faster than before, since all of the data is available in the plain to at least one of the parties.

As pointed out, there are many ways to determine the class in a log entry. For example, the class may be encrypted by the reader and decrypted during the first step of the analysis. The class can instead be determined during the first step of the analysis by performing a lookup of the, possibly encrypted, tag id into a lookup table.

Consider the following computation: hospital management wants to find out the patient/nurse ratio. One may first compute how many patients were in a specific room, and in a specific timeslot. The same may be done for the number of employees, e.g., nurses. Using generic multi-party computation this computation may need more work, especially if it is done for multiple rooms and/or timeslots. The full multi-party computation may comprise oblivious comparisons on encrypted room numbers and/or encrypted timeslots, comparisons on whether log entries belong to the same person, and comparison on whether that person is a patient or an employee. Finally, to find the ratio, a division may be performed on the two (encrypted) number of persons.

However, using the optimization using class attributes, this becomes a lot easier. The first step of processing above can be done using multi-party computation. There is only a single comparison, e.g., patient/employee, necessary for every entry in the log, and that comparison may even be performed without encryption.

The second step becomes simpler: the controlling party computation server has all employee data in the plain, and can simply count the number of employees in the specific room at the specific timeslot. The management computation server can do the same. A multi-party division protocol may be used to find the ratio. Note that, even though the computation is performed on the controlling part's computer, the computation itself may be provided by the managing party. A controlling party may verify that the code does not contain inadvertent leaking of information by inspection.

In addition to hospitals, embodiments may be employed in many situations. Examples include tracking of customers in a shop, tracking of assets through a third-party manufacturing plant, etc.

Figure 3:
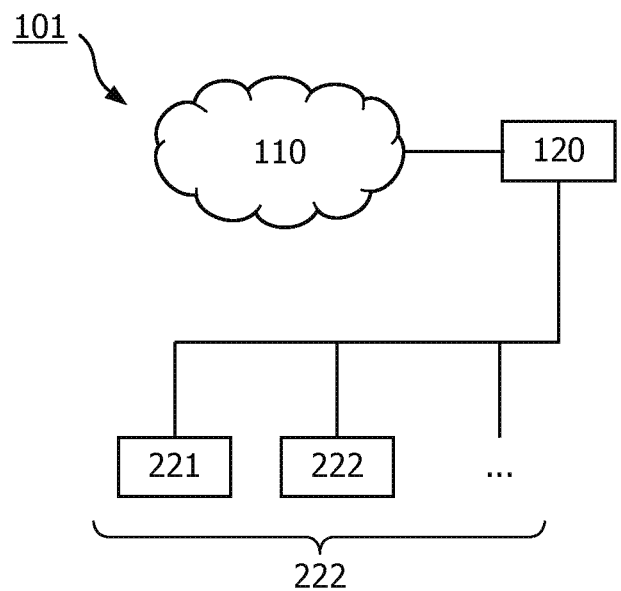

FIG. 3 schematically shows an example of an embodiment of a location-tracking system 101. In system 101, all location analysis devices are connected, e.g., receive location updates from the location database 120. Shown are two connected location analysis devices 221, 222, there may be more.

Figure 4:
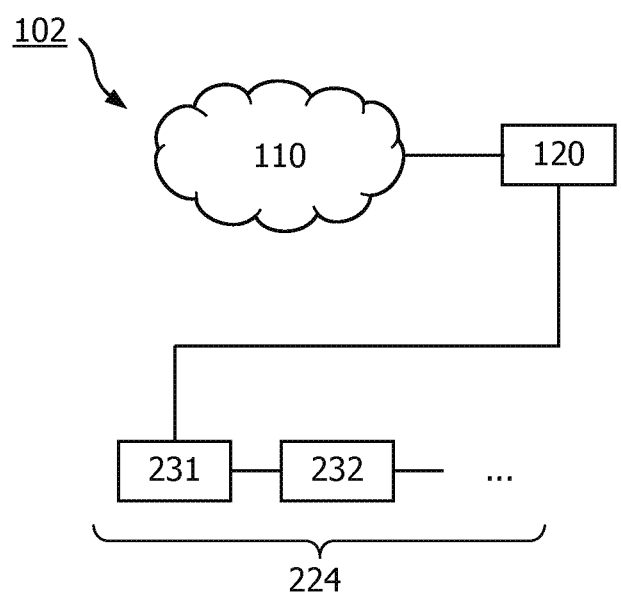

FIG. 4 schematically shows an example of an embodiment of a location-tracking system 102. In system 102, not all location analysis device are connected, one location analysis device receives location updates from the location database 120, and some receive location updates from another location analysis device. In the example shown in FIG. 4, location analysis device 231 is connected, but location analysis device 232 is unconnected. Additional unconnected location analysis device could be added.

Both situations may use various types of multi-party computation. For example, a system as in FIG. 3 may be converted to one as in FIG. 4, by simply forwarding the location updates. Likewise, FIG. 4 may be regarded as a special case of a connected system, in which the receiving of location updates is a first step of the multi-party computation. Below two examples, are given, one in the context of FIG. 3, and one in the context of FIG. 4, though each could be adapted to the other situation.

Example 1 (FIG. 3). The location updates in database 120 may be encrypted with a threshold homomorphic encryption scheme, e.g., Paillier encryption or ElGamal encryption. The location updates in database 120 may be encrypted with a public database encryption key. Devices 221, 222, . . . , each have a key-share in the private key. The fully encrypted location updates may be retrieved by the location analysis devices. Using the homomorphic property computations can then be performed on the encrypted location updates. An example, of a multi-party computation scheme using a Threshold Homomorphic Encryption is give in "Multiparty Computation from Threshold Homomorphic Encryption", by Ronald Cramer, et al.

Example 2 (FIG. 4). The location updates in database 120 may be encrypted with two stream ciphers. For example, consider a database encryption key that comprises multiple subkeys: $K=(K_1, K_2, \ldots)$. Using the subkeys a pseudorandom stream may be generated, e.g., using a blockcipher, e.g., AES, in counter mode. For example, a location update may be encrypted as $L+E_{K_1}+E_{K_2}$, in which L represents the plain location update, $E_{K_1}$ represents a stream generated from $K_1$, and $E_{K_2}$ represents a stream generated from $K_2$. Device 231 has access to key $K_1$; device 232 has access to key $K_2$. For example, device 231 may retrieve a fully encrypted location update. Device 231 may then compute $E_{K_1}$ itself, and from that compute $L+E_{K_2}$, that is a partially decrypted location update. Device 231 then enters the partially decrypted location update in the multi-party computation, but as a private input. For example, device 231 may compute shares $L_i$ for the location updates, in which i runs over the location analysis devices, and provide each location analysis device with a share. Device 232 computes $E_{K_2}$ and enters it as a private input in the computation, in the same way. If there are more location analysis devices, then each may compute the encrypting stream $E_{K_i}$ from their share $K_i$. The multi-party computation may then proceed with computing the location update from the inputs of the devices. This is an efficient computation, since only addition or subtractions are needed. For example, the addition may be implemented as an XOR, which means that it suffices to perform multi-party XOR to obtain a secret-shared decrypted location update. The multi-party computation type may, e.g., be Shamir or SPDZ. In this example, the computation related to the decryption operations, is performed almost fully locally without mpc interaction. This increases the efficiency of this option.

Example 3 (FIG. 4). As an alternative, the location updates may be encrypted with a block cipher using a single key K, using an appropriate block cipher mode; this may be a streaming mode such as counter mode, but may be any other mode, e.g., CBC. The key shares are chosen such that K can be computed form them, e.g., $K=K_1+K_2+\ldots$. In this case, all devices enter their key share as a private input into the computation. Device 231 also retrieves the encrypted location updates and enters them into the computation as a private input. The mpc can now proceed by computing the secret-shared key K, and decrypting the location update with it. The latter computation being entirely within the mpc. Example 3 is less efficient than example 2, but it has the advantage that is compatible with standard encryption, e.g., block cipher encryption, e.g., a standard AES in a standard block cipher mode.

In example 2 above, the streams $E_{K_i}$, i≥2 may be regarded as decryption information. In example 3 above, the key shares $K_i$, i≥2 may be regarded as a decryption information. In both cases, the decryption information is computed from a key share and entered as a private input to facilitate decrypting the location updates in the multi-party computation.

Figure 5:
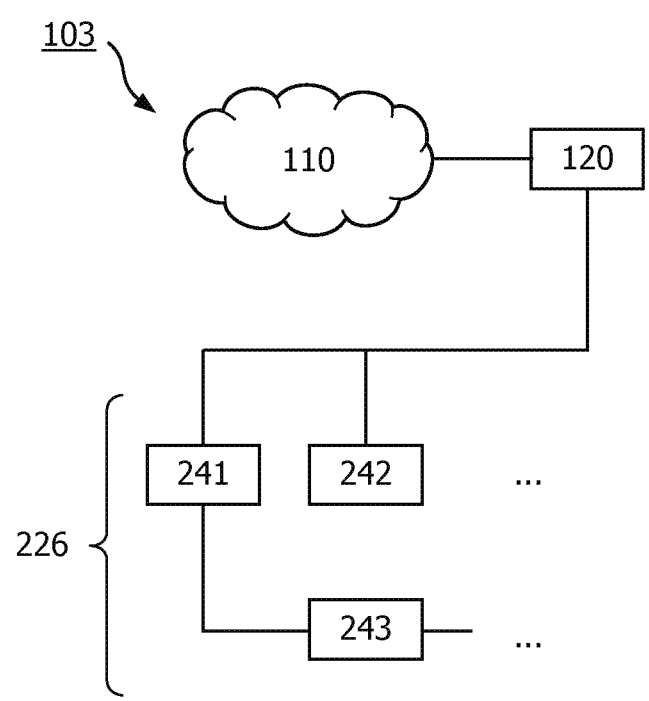

FIG. 5 schematically shows an example of an embodiment of a location-tracking system 103. More than one device is connected, and one or more devices are unconnected. For example, any of the examples above may be adopted to the situation of FIG. 5. Shown are connected devices 241, 242 and unconnected device 243.

In the various embodiments of location analysis devices, e.g., devices 201-202, 221-222, 231-232, 241-243, the communication interface may be selected from various alternatives. For example, the interface may be a network interface to a local or wide area network, e.g., the Internet, a storage interface to an internal or external data storage, an application interface (API), etc. The location analysis devices may have a user interface, which may include well-known elements such as one or more buttons, a keyboard, display, touch screen, etc. The user interface may be arranged for accommodating user interaction for performing a multi-party computation, or entering an authorization, or receiving an analysis result, etc.

Storage in the location analysis devices may be implemented as an electronic memory, say a flash memory, or magnetic memory, say hard disk or the like, or optical memory, e.g., a DVD. Storage may comprise multiple discrete memories together making up storage. Storage may comprise a temporary memory, say a RAM.

Typically, the location analysis devices each comprise a microprocessor which executes appropriate software stored at the device; for example, that software may have been downloaded and/or stored in a corresponding memory, e.g., a volatile memory such as RAM or a non-volatile memory such as Flash. The tracking devices and database device may also be equipped with microprocessors and memories. Alternatively, the location analysis devices may, in whole or in part, be implemented in programmable logic, e.g., as field-programmable gate array (FPGA). Location analysis devices may be implemented, in whole or in part, as a so-called application-specific integrated circuit (ASIC), e.g., an integrated circuit (IC) customized for their particular use. For example, the circuits may be implemented in CMOS, e.g., using a hardware description language such as Verilog, VHDL etc.

In an embodiment, the location analysis devices comprise a communication circuit, and a multi-party computation circuit. The circuits implement the corresponding functions described herein. The circuits may be a processor circuit and storage circuit, the processor circuit executing instructions represented electronically in the storage circuits.

A processor circuit may be implemented in a distributed fashion, e.g., as multiple sub-processor circuits. A storage may be distributed over multiple distributed sub-storages. Part or all of the memory may be an electronic memory, magnetic memory, etc. For example, the storage may have volatile and a non-volatile part. Part of the storage may be read-only.

Figure 6A:
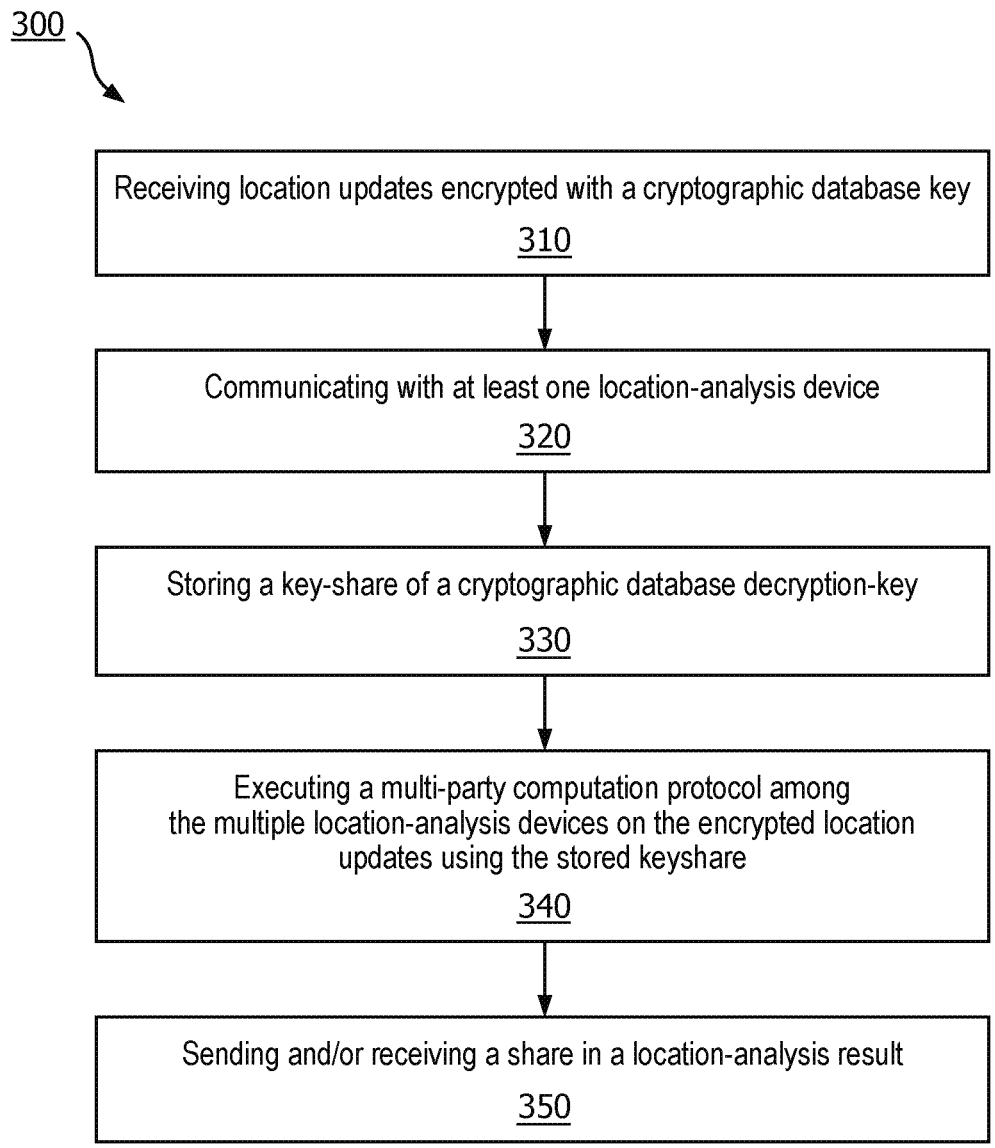

FIG. 6a schematically shows an example of an embodiment of a location analysis method 300. Location analysis method 300 may comprise receiving (310) location updates encrypted with a cryptographic database key from a location database, the location database being configured to receive a plurality of location updates from a plurality of tracking devices, the plurality of location updates indicating the location of one or more objects, communicating (320) with at least one location-analysis device of multiple location-analysis devices, storing (330) a key-share of a cryptographic database decryption-key corresponding to the cryptographic database encryption-key, said cryptographic database decryption-key being shared into multiple key-shares stored at the multiple location-analysis devices, executing (340) a multi-party computation protocol among the multiple location-analysis devices on the encrypted location updates using the stored key-share, thus jointly computing a location-analysis result secret-shared among the multiple location analysis devices, sending and/or receiving (350) a share in the location-analysis result for opening the location-analysis result.

Figure 6B:
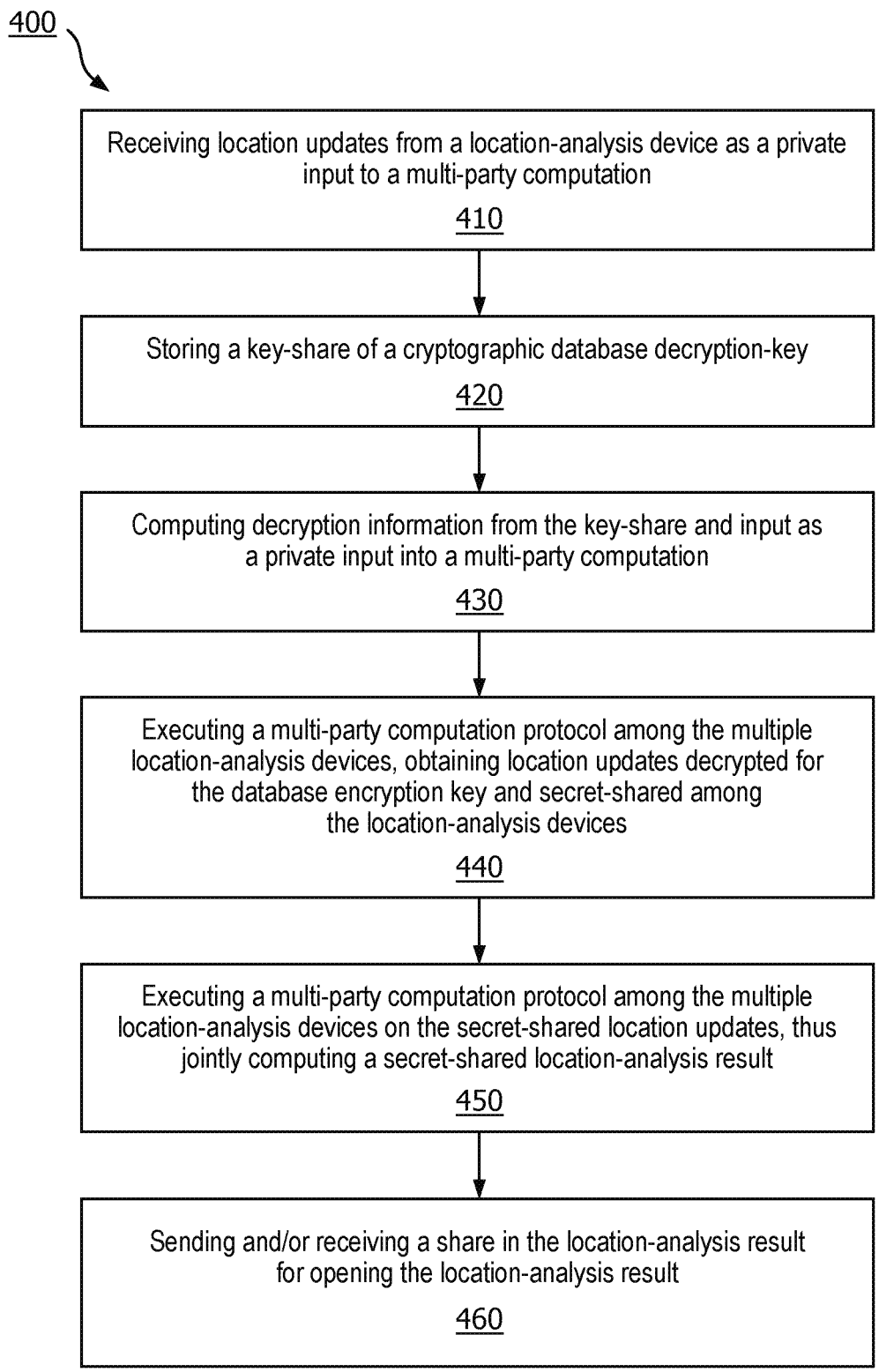

FIG. 6*b* schematically shows an example of an embodiment of a location analysis method 400. Location analysis method 400 may comprise

- receiving (410) location updates from another location-analysis device as a private input to a multi-party computation, the location updates being location updates that were encrypted with a cryptographic database key from a location database and partially decrypted with a key-share of the other location-analysis device,
- storing (420) a key-share of a cryptographic database decryption-key corresponding to the cryptographic database encryption-key, said cryptographic database decryption-key being shared into multiple key-shares stored at multiple location-analysis devices,
- computing (430) decryption information from the key-share of the unconnected location-analysis device and input the decryption information as a private input into the multi-party computation,
- executing (440) a multi-party computation protocol on the secret-shared location-updates and the secret-shared decryption information with at least the other location-analysis device to obtain location updates decrypted for the database encryption key and secret-shared among the location-analysis devices,
- executing (450) a multi-party computation protocol among the multiple location-analysis devices on the secret-shared location updates, thus jointly computing a secret-shared location-analysis result,
- sending and/or receiving (460) a share in the location-analysis result for opening the location-analysis result.

Many different ways of executing the method are possible, as will be apparent to a person skilled in the art. For example, the steps can be performed in the shown order, but the order of the steps may also be varied or some steps may be executed in parallel. Moreover, in between steps other method steps may be inserted. The inserted steps may represent refinements of the method such as described herein, or may be unrelated to the method. Moreover, a given step may not have finished completely before a next step is started. For example, methods 300 and 400 may comprise additional steps as set out herein. Methods 300 and 400 may be part of a tracking method, e.g., comprising receiving a plurality of location updates from a plurality of tracking devices, and/or encrypting the location updates with a cryptographic database encryption-key, etc.

Embodiments of the method may be executed using software, which comprises instructions for causing a processor system to perform method 300 or 400. Software may only include those steps taken by a particular sub-entity of the system. The software may be stored in a suitable storage medium, such as a hard disk, a floppy, a memory, an optical disc, etc. The software may be sent as a signal along a wire, or wireless, or using a data network, e.g., the Internet. The software may be made available for download and/or for remote usage on a server. Embodiments of the method may be executed using a bitstream arranged to configure programmable logic, e.g., a field-programmable gate array (FPGA), to perform the method.

It will be appreciated that the invention also extends to computer programs, particularly computer programs on or in a carrier, adapted for putting the invention into practice. The program may be in the form of source code, object code, a code intermediate source, and object code such as partially compiled form, or in any other form suitable for use in the implementation of an embodiment of the method. An embodiment relating to a computer program product comprises computer executable instructions corresponding to each of the processing steps of at least one of the methods set forth. These instructions may be subdivided into subroutines and/or be stored in one or more files that may be linked statically or dynamically. Another embodiment relating to a computer program product comprises computer executable instructions corresponding to each of the means of at least one of the systems and/or products set forth.

Figure 7A:
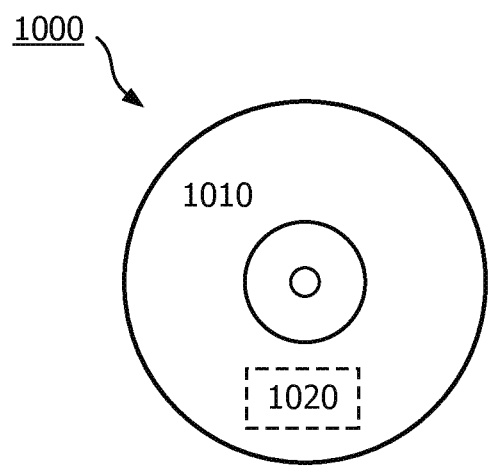

FIG. 7*a* shows a computer readable medium 1000 having a writable part 1010 comprising a computer program 1020, the computer program 1020 comprising instructions for causing a processor system to perform a location analysis method according to an embodiment. The computer program 1020 may be embodied on the computer readable medium 1000 as physical marks or by means of magnetization of the computer readable medium 1000. However, any other suitable embodiment is conceivable as well. Furthermore, it will be appreciated that, although the computer readable medium 1000 is shown here as an optical disc, the computer readable medium 1000 may be any suitable computer readable medium, such as a hard disk, solid state memory, flash memory, etc., and may be non-recordable or recordable. The computer program 1020 comprises instructions for causing a processor system to perform said location analysis method.

Figure 7B:
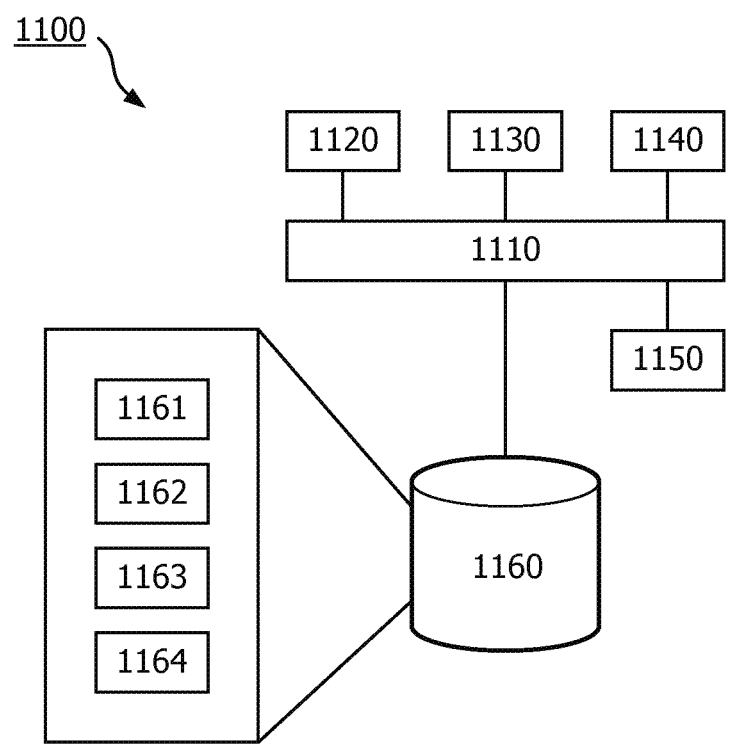

FIG. 7*b* illustrates an exemplary hardware diagram 1100 for implementing a device according to an embodiment, e.g., a location analysis device, e.g., a connected or unconnected location analysis device. The exemplary hardware 1100 may correspond to one or more location analysis devices of FIGS. 1-5. As shown, the device 1100 includes a processor 1120, memory 1130, user interface 1140, communication interface 1150, and storage 1160 interconnected via one or more system buses 1110. It will be understood that this figure constitutes, in some respects, an abstraction and that the actual organization of the components of the device 1100 may be more complex than illustrated.

The processor 1120 may be any hardware device capable of executing instructions stored in memory 1130 or storage 1160 or otherwise processing data. As such, the processor may include a microprocessor, field programmable gate array (FPGA), application-specific integrated circuit (ASIC), or other similar devices. For example, the processor may be an Intel Core i7 processor, ARM Cortex-R8, etc. In an embodiment, the processor may be ARM Cortex M0.

The memory 1130 may include various memories such as, for example L1, L2, or L3 cache or system memory. As such, the memory 1130 may include static random access memory (SRAM), dynamic RAM (DRAM), flash memory, read only memory (ROM), or other similar memory devices. It will be apparent that, in embodiments where the processor includes one or more ASICs (or other processing devices) that implement one or more of the functions described herein in hardware, the software described as corresponding to such functionality in other embodiments may be omitted.

The user interface 1140 may include one or more devices for enabling communication with a user such as an administrator. For example, the user interface 1140 may include a display, a mouse, and a keyboard for receiving user commands. In some embodiments, the user interface 1140 may include a command line interface or graphical user interface that may be presented to a remote terminal via the communication interface 1150.

The communication interface 1150 may include one or more devices for enabling communication with other hardware devices. For example, the communication interface 1150 may include a network interface card (NIC) configured to communicate according to the Ethernet protocol. For example, the communication interface 1150 may comprise an antenna, connectors or both, and the like. Additionally, the communication interface 1150 may implement a TCP/IP stack for communication according to the TCP/IP protocols. Various alternative or additional hardware or configurations for the communication interface 1150 will be apparent.

The storage 1160 may include one or more machine-readable storage media such as read-only memory (ROM), random-access memory (RAM), magnetic disk storage media, optical storage media, flash-memory devices, or similar storage media. In various embodiments, the storage 1160 may store instructions for execution by the processor 1120 or data upon with the processor 1120 may operate. For example, the storage 1160 may store a base operating system 1161 for controlling various basic operations of the hardware 1100. For example, the storage may store instructions 1162 for a location analysis device to execute a multi-party computation protocol, etc.

It will be apparent that various information described as stored in the storage 1160 may be additionally or alternatively stored in the memory 1130. In this respect, the memory 1130 may also be considered to constitute a "storage device" and the storage 1160 may be considered a "memory." Various other arrangements will be apparent. Further, the memory 1130 and storage 1160 may both be considered to be "non-transitory machine-readable media." As used herein, the term "non-transitory" will be understood to exclude transitory signals but to include all forms of storage, including both volatile and non-volatile memories.

While device 1100 is shown as including one of each described component, the various components may be duplicated in various embodiments. For example, the processor 1120 may include multiple microprocessors that are configured to independently execute the methods described herein or are configured to perform steps or subroutines of the methods described herein such that the multiple processors cooperate to achieve the functionality described herein. Further, where the device 1100 is implemented in a cloud computing system, the various hardware components may belong to separate physical systems. For example, the processor 1120 may include a first processor in a first server and a second processor in a second server.

It should be noted that the above-mentioned embodiments illustrate rather than limit the invention, and that those skilled in the art will be able to design many alternative embodiments.

In the claims, any reference signs placed between parentheses shall not be construed as limiting the claim. Use of the verb 'comprise' and its conjugations does not exclude the presence of elements or steps other than those stated in a claim. The article 'a' or 'an' preceding an element does not exclude the presence of a plurality of such elements. Expressions such as "at least one of" when preceding a list of elements represent a selection of all or of any subset of elements from the list. For example, the expression, "at least one of A, B, and C" should be understood as including only A, only B, only C, both A and B, both A and C, both B and C, or all of A, B, and C. The invention may be implemented by means of hardware comprising several distinct elements, and by means of a suitably programmed computer. In the device claim enumerating several means, several of these means may be embodied by one and the same item of hardware. The mere fact that certain measures are recited in mutually different dependent claims does not indicate that a combination of these measures cannot be used to advantage.

In the claims references in parentheses refer to reference signs in drawings of exemplifying embodiments or to formulas of embodiments, thus increasing the intelligibility of the claim. These references shall not be construed as limiting the claim.

The invention claimed is:

1. A location-tracking system comprising
   a location database configured to receive a plurality of location updates from a plurality of tracking devices, the plurality of location updates indicating the location of one or more objects, the location updates being stored encrypted with a cryptographic database encryption-key,
   multiple location-analysis devices, one or more location-analysis devices of the multiple location-analysis devices comprising
      a communication interface arranged to receive location updates encrypted with the cryptographic database key from the location database, and to communicate with at least one other location-analysis device of the multiple location-analysis devices,
      a key storage configured to store a key-share of a cryptographic database decryption-key corresponding to the cryptographic database encryption-key, said cryptographic database decryption-key being shared into multiple key-shares stored at the multiple location-analysis devices,
      a processor configured to
         execute a multi-party computation protocol among the multiple location-analysis devices on the encrypted location updates using the stored key-share, thus jointly computing a location-analysis result secret-shared among the multiple location analysis devices, wherein the multi-party computation protocol comprises multiple oblivious comparisons between an encrypted location update and an input-location, and
         send and/or receive a share in the location-analysis result for opening the location-analysis result.

2. The location-tracking system as in claim 1, wherein the multiple location-analysis devices comprise one or more connected location-analysis devices and one or more unconnected location-analysis devices, wherein
   the communication interface of a connected location-analysis devices is arranged to receive location updates encrypted with the cryptographic database key from the location database, and the communication interface of an unconnected location-analysis devices is arranged to receive location updates from another location-analysis device, wherein
   the processor of a connected location-analysis device is arranged to
      partially decrypt the received location updates with a key-share of the connected location-analysis device obtaining partially encrypted location updates,
      input the partially encrypted location updates into the multi-party computation,
      execute a multi-party computation protocol with the location-analysis devices to obtain location updates decrypted for the database encryption key and secret-shared among the location-analysis devices, and
   the processor of an unconnected location-analysis device is arranged to compute decryption information from the key-share of the unconnected location-analysis device and input the decryption information as a private input into the multi-party computation, execute a multi-party computation protocol on the secret-shared location-updates and the secret-shared decryption information with the location-analysis devices to obtain location updates decrypted for the database encryption key and secret-shared among the location-analysis devices.

3. A connected location-analysis device comprising a communication interface arranged to receive location updates encrypted with a cryptographic database key from a location database, and to communicate with at least one other location-analysis device of multiple location-analysis devices, the location database being configured to receive a plurality of location updates from a plurality of tracking devices, the plurality of location updates indicating the location of one or more objects, a key storage configured to store a key-share of a cryptographic database decryption-key corresponding to the cryptographic database encryption-key, said cryptographic database decryption-key being shared into multiple key-shares stored at the multiple location-analysis devices, a processor configured to execute a multi-party computation protocol among the multiple location-analysis devices on the encrypted location updates using the stored key-share, thus jointly computing a location-analysis result secret-shared among the multiple location analysis devices, wherein the multi-party computation protocol comprises multiple oblivious comparisons between an encrypted location update and an input-location, and send and/or receive a share in the location-analysis result for opening the location-analysis result.

4. The connected location-analysis device as in claim 3, wherein the database encryption-key and the key-shares of the database decryption-key are according to a threshold homomorphic encryption scheme.

5. The location-analysis device as in claim 3, wherein the multi-party computation protocol comprises counting location updates at or near an input-location.

6. The location-analysis device as in claim 3, wherein the communication interface is arranged to receive an authorization input, and the processor is configured to allow execution of the multi-party computation protocol before receiving the authorization input and to require receiving the authorization input before computing or sending the share in the decrypted location-analysis result for opening the encrypted location-analysis result.

7. The location-analysis device as in claim 3, wherein a location update comprises a class attribute, the location-analysis device being associated with one or more particular values of the class attribute, wherein the multi-party computation protocol comprises joint decryption for the location-analysis device of location updates wherein the class attribute equals one of the one or more particular values, wherein location-analysis devices associated with the one or more particular values obtain the decrypted location updates the multi-party protocol comprising performing a computation by the location-analysis device associated with the one or more particular values on the decrypted location updates that comprise the one or more particular class attribute values, obtaining a plain computation result, entering the computation result into the multi-party computation as a private input, the location-analysis result depending on the computation result.

8. The location-analysis device as in claim 7, wherein at least one further location-analysis device is associated with the one or more particular values of the class attribute, the computation being performed by the multiple location-analysis devices associated with the one or more particular values on the decrypted location updates, obtaining multiple plain computation results, the location-analysis device being configured for entering the multiple computation results into multiple multi-party computations by sharing the computation results with one or more location-analysis devices, obtaining multiple secret-shared location-analysis results from the multiple multi-party computations, each one of the multiple location-analysis results depending on a respective one of the multiple computation results, opening the multiple secret-shared location-analysis results and comparing the equality of the multiple opened location-analysis results.

9. The location-analysis device as in claim 7, wherein the class attribute is unencrypted in the location database, or the class attribute is encrypted with the database encryption-key, the multi-party computation protocol comprising a joint decryption of the class attribute by the multiple location-analysis devices.

10. The location-analysis device as in claim 7, wherein the location updates comprise dummy location updates for at least some of the one or more particular values of the class attribute, the processor being configured to discard the dummy location updates after obtaining the decrypted location updates.

11. The location-analysis device as in claim 7, wherein the multi-party computation protocol comprises counting location updates at or near an input-location of location updates comprising one or more particular class attributes, the counting being done on plain location updates.

12. The location-analysis device as in claim 11, wherein the multi-party computation comprises performing a multi-party division on two or more secret-shared values obtained from counting plain location updates.

13. The location-analysis device as in claim 3, wherein the plurality of tracking devices comprise a reader arranged to detect the presence and absence of tags in an area surrounding the reader, said readers being configured to send a digital signal to enable storage of the encrypted location updates, wherein the plurality of tracking devices are installed at fixed locations, and the tags are affixed to the one or more objects, or the plurality of tracking devices are affixed to the one or more objects, and the tags are installed at fixed locations.

14. The location-analysis device as in claim 3, wherein more than one key share of the database decryption-key is required for decryption of a location update, and wherein a location-analysis device stores fewer key shares than required for decryption of a location update.

15. The location-analysis device as in claim 3, wherein the tracking devices are arranged in a hospital and/or wherein a location update comprises a class attribute which at least indicates whether the location update corresponds to an employee or to a patient.

16. An unconnected location-analysis device comprising
a communication interface arranged to receive location updates from another location-analysis device as a private input to a multi-party computation, the location updates being location updates that were encrypted with a cryptographic database key from a location database and partially decrypted with a key-share of the other location-analysis device,
a key storage configured to store a key-share of a cryptographic database decryption-key corresponding to the cryptographic database encryption-key, said cryptographic database decryption-key being shared into multiple key-shares stored at multiple location-analysis devices,
a processor configured to
compute decryption information from the key-share of the unconnected location-analysis device and input the decryption information as a private input into the multi-party computation,
execute a multi-party computation protocol with at least the other location-analysis device to obtain location updates decrypted for the database encryption key and secret-shared among the location-analysis devices,
execute a multi-party computation protocol among the multiple location-analysis devices on the secret-shared location updates, thus jointly computing a secret-shared location-analysis result, wherein the multi-party computation protocol comprises multiple oblivious comparisons between an encrypted location update and an input-location, and
send and/or receive a share in the location-analysis result for opening the location-analysis result.

17. The unconnected location-analysis device as in claim 16, wherein the location updates are stored encrypted with a stream cipher.

18. A location analysis method comprising
receiving location updates encrypted with a cryptographic database key from a location database, the location database being configured to receive a plurality of location updates from a plurality of tracking devices, the plurality of location updates indicating the location of one or more objects,
communicating with at least one location-analysis device of multiple location-analysis devices,
storing a key-share of a cryptographic database decryption-key corresponding to the cryptographic database encryption-key, said cryptographic database decryption-key being shared into multiple key-shares stored at the multiple location-analysis devices,
executing a multi-party computation protocol among the multiple location-analysis devices on the encrypted location updates using the stored key-share, thus jointly computing a location-analysis result secret-shared among the multiple location analysis devices, wherein the multi-party computation protocol comprises multiple oblivious comparisons between an encrypted location update and an input-location, and
sending and/or receiving a share in the location-analysis result for opening the location-analysis result.

* * * * *